(12) United States Patent
Smith et al.

(10) Patent No.: US 6,972,017 B2
(45) Date of Patent: *Dec. 6, 2005

(54) POLYPECTOMY SNARE HAVING ABILITY TO ACTUATE THROUGH TORTUOUS PATH

(75) Inventors: Kevin W. Smith, Coral Gables, FL (US); Sean McBrayer, Miami, FL (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/345,519

(22) Filed: Jan. 16, 2003

(65) Prior Publication Data

US 2003/0125731 A1 Jul. 3, 2003

Related U.S. Application Data

(63) Continuation of application No. 09/716,776, filed on Nov. 20, 2000, now Pat. No. 6,517,539, which is a continuation-in-part of application No. 09/369,724, filed on Aug. 6, 1999, now Pat. No. 6,235,026.

(51) Int. Cl.$^7$ ............................................. A61B 18/18
(52) U.S. Cl. ...................................... 606/47; 606/113
(58) Field of Search ........................... 606/46, 47, 110, 606/113, 114

(56) References Cited

U.S. PATENT DOCUMENTS

| | | |
|---|---|---|
| 1,127,948 A | 2/1915 | Wappler |
| 2,036,528 A | 4/1936 | Kesling |
| 2,950,609 A | 8/1960 | Goodloe |
| 3,554,192 A | 1/1971 | Isberner |
| 3,895,636 A | 7/1975 | Schmidt |
| 3,955,578 A | 5/1976 | Chamness et al. |
| 4,256,113 A * | 3/1981 | Chamness .................... 606/47 |
| 4,294,254 A | 10/1981 | Chamness |
| 4,326,530 A | 4/1982 | Fleury, Jr. |
| 4,327,711 A | 5/1982 | Takagi |
| 4,345,599 A | 8/1982 | McCarrell |
| 4,430,083 A | 2/1984 | Ganz et al. |
| 4,493,320 A | 1/1985 | Treat |
| 4,503,855 A | 3/1985 | Maslanka |
| 4,590,938 A | 5/1986 | Segura et al. |
| 4,593,680 A | 6/1986 | Kubokawa |

(Continued)

FOREIGN PATENT DOCUMENTS

DE 28 29 159 A1 1/1980

(Continued)

OTHER PUBLICATIONS

Product Brochure, "Trio 14, Re-engineering Over-the-Wire Balloon Technology," 1994, 4 pages.

Primary Examiner—Michael Peffley
(74) Attorney, Agent, or Firm—Crompton, Seager & Tufte, LLC

(57) ABSTRACT

This invention relates broadly to surgical instruments. More particularly, this invention relates to a surgical snare instrument for excising polyps. Preferably, the instrument includes a coupling member that may increase ability to actuate the snare. According to a preferred embodiment, the present invention comprises a surgical instrument for insertion through an endoscope having a handle and a working channel, said surgical instrument including an elongate flexible tubular sheath having proximal and distal ends; a flexible shaft extending through and axially movable relative to the sheath, said shaft having proximal and distal ends; an end effector coupled to or formed at said distal end of said shaft; and a coupling member disposed at said distal end of said shaft.

22 Claims, 5 Drawing Sheets

U.S. PATENT DOCUMENTS

| | | | |
|---|---|---|---|
| 4,619,260 A | 10/1986 | Magill et al. | |
| 4,632,110 A | 12/1986 | Sanagi | |
| 4,706,656 A | 11/1987 | Kuboto | |
| 4,763,668 A | 8/1988 | Macek et al. | |
| 4,785,825 A | 11/1988 | Romaniuk et al. | |
| 4,790,831 A | 12/1988 | Skribiski | |
| D301,614 S | 6/1989 | Kozak et al. | |
| 4,840,176 A | 6/1989 | Ohno | |
| 4,840,623 A | 6/1989 | Quackenbush | |
| 4,869,238 A | 9/1989 | Opie et al. | |
| 4,872,456 A | 10/1989 | Hasson | |
| 4,905,691 A | 3/1990 | Rydell | |
| 4,945,920 A | 8/1990 | Clossick | |
| 4,950,232 A | 8/1990 | Ruzicka et al. | |
| 4,967,732 A | 11/1990 | Inoue | |
| 4,973,321 A | 11/1990 | Michelson | |
| 5,005,755 A | 4/1991 | Takahashi et al. | |
| 5,026,371 A | 6/1991 | Rydell et al. | |
| 5,059,199 A | 10/1991 | Okada et al. | |
| 5,066,295 A | 11/1991 | Kozak et al. | |
| 5,084,054 A | 1/1992 | Bencini et al. | |
| 5,114,403 A | 5/1992 | Clark et al. | |
| 5,125,909 A | 6/1992 | Heimberger | |
| 5,129,913 A | 7/1992 | Ruppert | |
| 5,147,316 A | 9/1992 | Castillenti | |
| 5,147,373 A | 9/1992 | Ferzli | |
| RE34,110 E | 10/1992 | Opie, et al. | |
| 5,156,590 A | 10/1992 | Vilmar | |
| 5,158,561 A | 10/1992 | Rydell et al. | |
| 5,163,942 A | 11/1992 | Rydell | |
| 5,176,677 A | 1/1993 | Wuchinich | |
| 5,176,702 A | 1/1993 | Bales et al. | |
| 5,179,935 A | 1/1993 | Miyagi | |
| 5,183,470 A | 2/1993 | Wettermann | |
| 5,201,740 A | 4/1993 | Nakao et al. | |
| 5,201,743 A | 4/1993 | Haber et al. | |
| 5,242,461 A * | 9/1993 | Kortenbach et al. | 606/159 |
| 5,244,619 A | 9/1993 | Burnham | |
| 5,254,117 A | 10/1993 | Rigby et al. | |
| 5,254,130 A | 10/1993 | Poncet et al. | |
| 5,279,280 A | 1/1994 | Bacich et al. | |
| 5,281,220 A | 1/1994 | Blake, III | |
| 5,281,230 A | 1/1994 | Heidmueller | |
| 5,290,294 A | 3/1994 | Cox et al. | |
| 5,318,564 A | 6/1994 | Eggers | |
| 5,334,169 A | 8/1994 | Brown et al. | |
| 5,336,227 A | 8/1994 | Nakao et al. | |
| 5,358,493 A | 10/1994 | Schweich, Jr. | |
| 5,376,094 A | 12/1994 | Kline | |
| 5,403,342 A | 4/1995 | Tovey et al. | |
| 5,404,887 A | 4/1995 | Prather | |
| 5,406,939 A | 4/1995 | Bala | |
| 5,439,478 A | 8/1995 | Palmer | |
| 5,465,710 A | 11/1995 | Miyagi | |
| 5,486,182 A | 1/1996 | Nakao et al. | |
| 5,496,292 A | 3/1996 | Burnham | |
| 5,501,692 A | 3/1996 | Riza | |
| 5,542,948 A | 8/1996 | Weaver et al. | |
| 5,584,843 A | 12/1996 | Wulfman et al. | |
| 5,588,964 A | 12/1996 | Imran et al. | |
| 5,591,202 A | 1/1997 | Slater et al. | |
| 5,601,533 A | 2/1997 | Hancke et al. | |
| 5,647,846 A | 7/1997 | Berg et al. | |
| 5,681,296 A | 10/1997 | Ishida | |
| 5,718,360 A | 2/1998 | Green et al. | |
| 5,741,271 A | 4/1998 | Nakao et al. | |
| 5,746,747 A | 5/1998 | McKeating | |
| 5,755,724 A | 5/1998 | Yoon | |
| 5,759,187 A | 6/1998 | Nakao et al. | |
| 5,762,631 A | 6/1998 | Klein | |
| 5,766,217 A | 6/1998 | Christy | |
| 5,769,841 A | 6/1998 | Odell et al. | |
| 5,792,116 A | 8/1998 | Berg et al. | |
| 5,800,444 A | 9/1998 | Ridinger et al. | |
| 5,814,052 A | 9/1998 | Nakao et al. | |
| 5,817,111 A | 10/1998 | Riza | |
| 5,820,464 A | 10/1998 | Parlato | |
| 5,827,177 A | 10/1998 | Omeda et al. | |
| 5,827,272 A | 10/1998 | Breining et al. | |
| 5,846,248 A | 12/1998 | Chu et al. | |
| 5,860,975 A | 1/1999 | Goble et al. | |
| 5,882,347 A | 3/1999 | Mouris-Laan | |
| 5,885,508 A | 3/1999 | Ishida | |
| 5,906,620 A | 5/1999 | Nakao et al. | |
| 5,906,621 A | 5/1999 | Secrest et al. | |
| 5,957,932 A | 9/1999 | Bates et al. | |
| 5,961,511 A | 10/1999 | Mortier et al. | |
| 5,971,994 A | 10/1999 | Fritzsch | |
| 5,984,904 A | 11/1999 | Steen et al. | |
| 5,984,920 A | 11/1999 | Steinbach | |
| 5,989,247 A | 11/1999 | Chambers | |
| 5,993,474 A | 11/1999 | Ouchi | |
| 6,001,096 A | 12/1999 | Bissinger et al. | |
| 6,010,512 A | 1/2000 | Chu et al. | |
| 6,015,381 A | 1/2000 | Ouchi | |
| 6,015,415 A | 1/2000 | Avellanet | |
| 6,024,708 A | 2/2000 | Bales et al. | |
| 6,027,460 A | 2/2000 | Shturman | |
| 6,050,995 A | 4/2000 | Durgin | |
| 6,068,603 A | 5/2000 | Suzuki | |
| 6,071,233 A | 6/2000 | Ishikawa et al. | |
| 6,074,408 A | 6/2000 | Freeman | |
| 6,090,073 A | 7/2000 | Gill | |
| 6,090,129 A | 7/2000 | Ouchi | |
| 6,093,195 A | 7/2000 | Ouchi | |
| 6,235,026 B1 | 5/2001 | Smith | |
| 6,264,664 B1 * | 7/2001 | Avellanet | 606/128 |
| 6,299,612 B1 * | 10/2001 | Ouchi | 606/47 |
| 6,517,539 B1 | 2/2003 | Smith et al. | |
| 6,537,205 B1 | 3/2003 | Smith | |

FOREIGN PATENT DOCUMENTS

| | | |
|---|---|---|
| DE | 36 16 193 A1 | 11/1986 |
| DE | 199 53 359 A1 | 5/2000 |
| WO | WO 92/22254 | 12/1992 |
| WO | WO 00/42926 | 7/2000 |
| WO | WO 00/53107 | 9/2000 |
| WO | WO 01/10321 | 2/2001 |

* cited by examiner

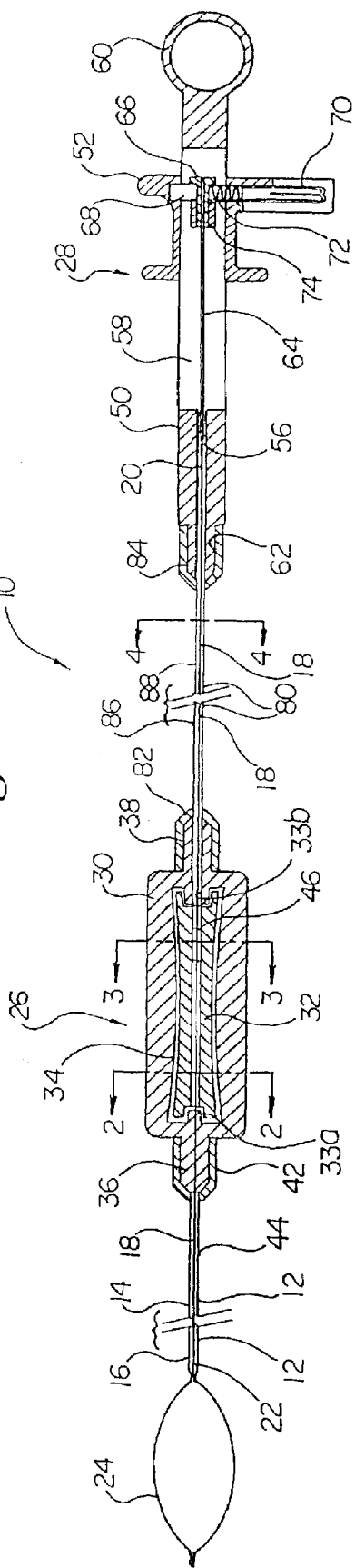
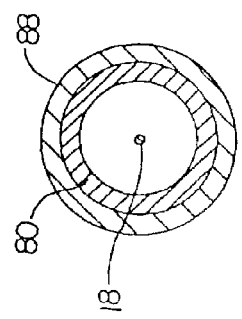
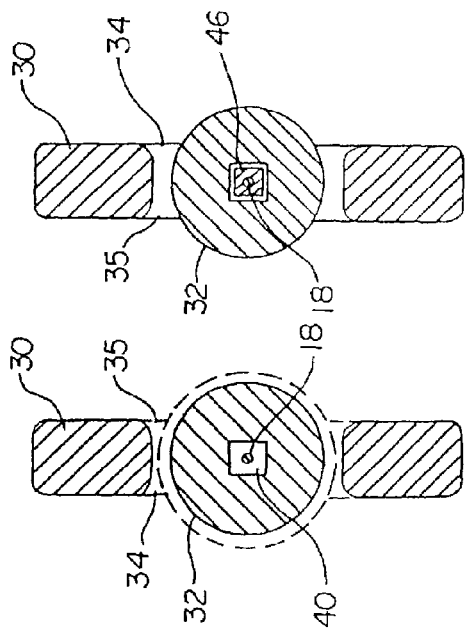
Fig. 1
Fig. 4
Fig. 3
Fig. 2

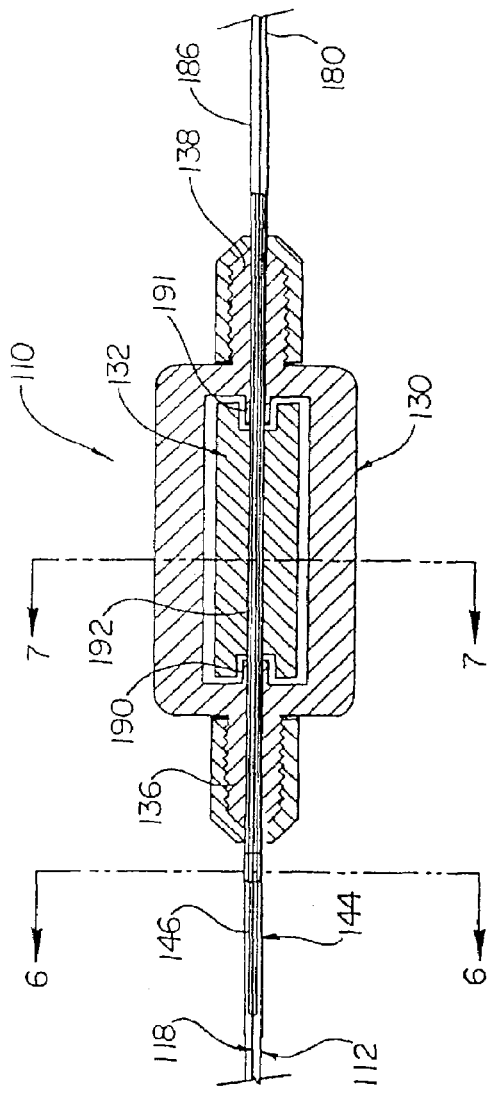
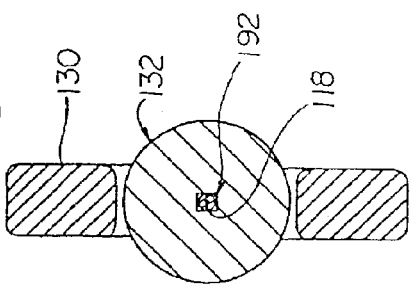
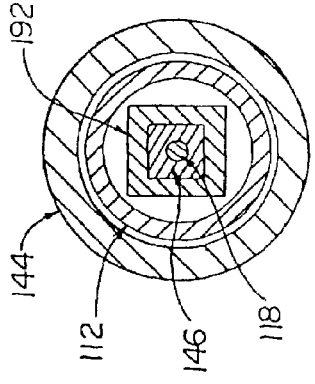

POLYPECTOMY SNARE HAVING ABILITY TO ACTUATE THROUGH TORTUOUS PATH

CROSS REFERENCE TO CO-PENDING APPLICATIONS

This application is a continuation of U.S. application Ser. No. 09/716,776, filed Nov. 20, 2000 now U.S. Pat. No. 6,517,539; which is a continuation-in-part of U.S. patent application Ser. No. 09/369,724, filed Aug. 6, 1999, U.S. Pat. No. 6,235,026 entitled Polypectomy Snare Instrument, the disclosure of which is hereby incorporated by reference.

FIELD OF THE INVENTION

This invention relates broadly to surgical instruments. More particularly, this invention relates to a surgical snare instrument for excising polyps. Preferably, the instrument includes a coupling member that may increase the ability to actuate the snare.

BACKGROUND OF THE INVENTION

Polypectomy snare instruments are used for the endoscopic removal of hypertrophic tissue growths within a body cavity, and particularly within the colon. Polypectomy snare instruments generally include an elongate tubular member, such as a catheter sheath, a shaft extending through the tubular member, an elastic wire forming a snare (loop) at the distal end of the shaft, and a handle for moving the shaft distally and proximally within the tubular member. The snare can be opened by moving the snare beyond the distal end of the sheath, and closed by retraction of the snare into the tubular member, each affected by movement of the shaft relative to the sheath.

In operation, a physician introduces the distal end of the instrument, with the snare of the snare instrument in a retracted position, through the working channel of an endoscope until the sheath begins to extend out of the distal end of the endoscope. The physician then directs an assistant, who has control of the handle of the snare instrument, to open the snare. The assistant accomplishes this function by moving two portions of the handle relative to each other. The physician then advances and retracts the sheath into and out of the endoscope, while applying torque to some portion of the instrument to position the snare loop over and around a polyp. Once the snare loop is positioned around the polyp, the physician orders the assistant to close the snare around the polyp. Then, the physician or assistant energizes a source of electrocautery current coupled to the shaft to desiccate, sever, and cauterize the polyp. Finally, the polyp is removed by withdrawing the snare (or, in some cases, the polyp is retrieved by use of another instrument such as a biopsy forceps). In a variation of the procedure, the physician uses suction applied to a channel of the endoscope to remove the polyp or to hold it to the end of the endoscope.

Prior art snare instruments have several problems. First, it is difficult for the physician to precisely position the snare because the physician relies on gripping the small, slippery sheath over the shaft near where the sheath enters the endoscope handle. Typically, it is necessary for the physician to repeatedly push, pull, and torque the sheath and the shaft of the instrument in order to achieve the desired position with the snare around the polyp. Second, the prior art instruments are not capable of efficient steering, because the shaft which is generally used is a cable having low torsional stiffness, and is not usually free of camber or "set". The result of these defects is that when the instrument is used in a tightly-flexed endoscope, the distal end of the snare does not respond directly to torsional input on the shaft where it enters the endoscope handle; i.e., rather than directly responding to torsional input from the physician, the shaft stores the torsional force and upon reaching a threshold, uncontrollable rotationally whips to release the force. Third, while several attempts have been made at providing a snare instrument with a handle adapted to more adeptly steer the snare, most of such prior art instruments do not specifically allow for rotating the snare to position it relative to the polyp. Rather, the physician must rotate the shaft of the instrument by tightly gripping and rotating the sheath where it enters the endoscope to try to maneuver the snare over the polyp. In addition, in the several prior art devices specifically adapted for rotational control, e.g., U.S. Pat. No. 5,066,295 to Kozak et al. and U.S. Pat. Nos. 3,955,587; 4,256,113; and 4,294,254 to Chamness et al., the rotational control function is placed in the handle at the proximal end of the instrument. This handle then controls the extension and retraction of the snare loop as well as the rotation of the snare loop. However, this handle is typically held by the assistant, so the physician must orally direct the assistant to coordinate the handle controls while the physician moves the jacket in and out of the endoscope. As a result, these instruments have not been widely accepted by physicians.

SUMMARY OF THE INVENTION

The invention provides a snare instrument which permits the physician to control all aspects of positioning the snare loop relative to the polyp, while allowing the assistant to perform the cauterizing and severing of the polyp. The snare instrument provides the physician the means for advancing and retracting the distal end of the snare instrument through the endoscope, as well as rotating the snare, and provides the assistant the means for extending and retracting the snare loop from the sheath of the snare instrument.

As described in detail below, a surgical snare instrument is provided. The snare instrument includes an elongate flexible tubular sheath, a flexible shaft extending through and axially movable relative to the sheath, a snare coupled to or formed at the distal end of the shaft, and a system to move the shaft, and consequently the snare, relative to the sheath. According to several embodiments of the invention, the system for moving the shaft relative to the sheath includes a first (physician's) handle capable of controlling the position of the snare, and a second (assistant's) handle proximal the first handle and adapted to control contraction of the snare and cauterization. The handles are coupled by a tubular sheath extension.

The physician's handle is preferably positioned along the sheath of the snare instrument so that it is a few inches proximal to the entry port of the endoscope handle when the distal end of the sheath is adjacent to the distal end of an endoscope. The physician's handle serves as a grippable element on the sheath and contains a rotating means for rotating the shaft, so that when the physician grips that handle the physician is capable of steering (rotating) the snare by operating the rotating means. In addition, the physician is also capable of positioning the entire sheath relative to the endoscope by sliding the sheath into and out of the working channel of the endoscope. The proximal handle is operable by an assistant and permits longitudinal movement of the shaft and snare and the application of a cautery current to the shaft and snare.

According to other embodiments, the snare instrument is provided with a connector which enables the snare instrument to be fixed relative to an endoscope handle. Additionally, an embodiment is also provided in which a single handle provides a physician with means for advancing and retracting the sheath of the snare instrument relative to the distal end of the endoscope, means for actuating or advancing (opening) and retracting (closing) the snare relative to the distal end of the sheath, and means for steering (rotating) the snare to position the snare over a polyp. Since the physician has direct and immediate control of the entire instrument, the snare instrument obviates the need for an assistant during the procedure, and improves the speed and efficiency of the polypectomy procedure.

In a preferred embodiment, the snare is coupled to or formed at the distal end of the shaft. Preferably, the snare is coupled to the shaft by a crimp band. In an exemplary embodiment a coupling member, for example a shrink tube, is disposed at the distal end of the shaft. The coupling member can be, for example, adhered to the shaft over the crimp band so that when the snare is actuated (e.g., retracted), the coupling member forms a gentle transition between the outer diameter of the shaft and the inner diameter of the sheath. Preferably, the coupling member increases the ability to actuate an end effector, for example, a snare. In an alternate embodiment, the coupling member can be adhered to the shaft just proximal of the crimp band so as to minimize the step in diameter when the snare is retracted.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation in section of a first embodiment of a snare instrument according to the invention;

FIG. 2 is an enlarged cross-section taken through line 2—2 in FIG. 1;

FIG. 3 is an enlarged cross-section taken through line 3—3 in FIG. 1;

FIG. 4 is an enlarged cross-section taken through line 4—4 in FIG. 1;

FIG. 5 is a broken section view of a physician's handle assembly according to the second embodiment of the snare instrument of the invention;

FIG. 6 is an enlarged cross-section through line 6—6 in FIG. 5, showing the engagement of a key in a knob shaft;

FIG. 7 is an enlarged cross-section through line 7—7 in FIG. 5, at a location proximal of the key;

DETAILED DESCRIPTION OF THE PREFERRED EMBODIMENTS

Figure 8:
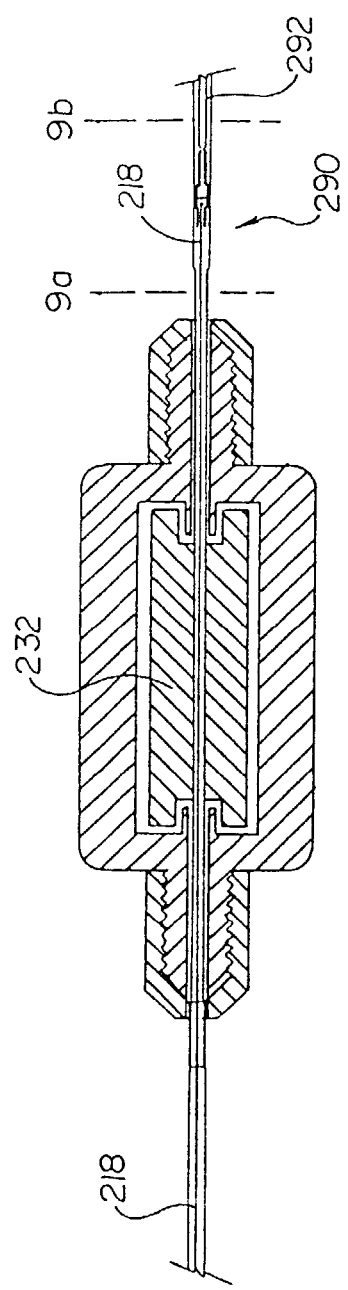
FIG. 8 is a broken section view of a third embodiment of the snare instrument according to the invention.

Turning now to FIG. 1, a first embodiment of a surgical snare instrument 10 according to the invention is shown. The snare instrument 10 includes an elongate flexible tubular sheath 12 having a proximal end 14 and a distal end 16, a flexible shaft 18 having a proximal end 20 and a distal end 22 extending through and axially movable relative to the sheath 12, a snare 24 coupled to or formed at the distal end 22 of the shaft 18, preferably adjacent the distal end 16 of the sheath 12, and first and second handle assemblies 26, 28, respectively, for moving the shaft 18 relative to the sheath 12.

The shaft 18 is preferably a high strength, straightened (camber-free) stainless steel wire of high elastic limit. The shaft 18 is adapted to be bent through a tortuous path without permanent deformation. In addition, since the shaft 18 is free of camber, it is possible to precisely rotate the snare 24 by rotating the shaft at any point along its length.

Referring now to FIGS. 1–3, the physician's handle assembly 26, which is the more distal of the two handles, generally includes a body 30 and a knob 32 mounted in the body 30 on bearings 33a, 33b in a manner which permits the knob 32 to rotate coaxially relative to the body. The body 30 includes a central bore 34 with one or more apertures 35, a threaded distal end 36, and a threaded proximal end 38. The sheath 12 of the snare instrument 10 is connected to the threaded distal end 36 of the body 32, e.g., by means of a flare-nut connection 42. Preferably, a stiffening sleeve 44 is provided over the sheath 12 at the connection 42. The knob 32 includes a non-circular bore 40, e.g., having the cross-sectional shape of a square. The knob 32 (for reasons discussed below) is preferably at least as long as the distance of movement required to open and close the snare 24; i.e., the length of the snare when compressed in the sheath 12. The apertures 35 provide access to the knob 32, so that the knob 32 can be rotated relative to the body 30, e.g., by a physician.

A portion of the shaft 18 extending through the bore 40 of the knob 32 is provided with a key 46; that is, a spline element fixed on and about the shaft 18 or, alternatively, rigidly and fixedly interposed between two portions of the shaft. The key 46 preferably has a rectangular shape but may have another non-circular shape. The key 46 is slidably axially movable within the bore 40. Therefore, the shaft 12 may be moved axially through the bore 40 (and that is why the length of the knob 32 is preferably at least as long as the distance of movement required to open and close the snare). However, when the knob 32 is rotated relative to the body 30, the key 46 within the bore 40 is rotated and, consequently, the shaft 18 and snare 24 are rotated relative to the sheath 12.

The distal handle assembly 28 is preferably positioned approximately 210 cm from the distal end 16 of the sheath 12 for a snare instrument 10 designed to be inserted into a 200 cm endoscope. Thus, the physician can grip the body 30 in a manner which permits rotating the knob 32 relative to the body, and hence the snare 24 relative to the sheath 12, while using the body 30 as a grip to axially position the snare instrument 10 within the working channel of an endoscope.

The shaft 18 extends out of the proximal end 38 of the body 30 to the proximal handle assembly 28, or assistant handle. The proximal handle assembly 28 preferably includes a stationary member 50 and a spool member 52 slidable relative to the stationary member. The stationary member 50 includes a longitudinal throughbore 56 which the proximal end 20 of the shaft 18 extends, a transverse slot 58, a proximal thumb ring 60, and a distal threaded connector 62. The proximal end of the shaft 18 is preferably provided with a conductive stiffening sleeve 64, and a cylindrical conductive bearing 66 is coupled about the proximal end of the stiffening sleeve 64. The spool member 62 includes a cross bar 68 which extends through the transverse slot 58 to secure the spool member 52 on the stationary member 50. In addition, the spool member 62 preferably includes a cautery plug 70. The conductive bearing 66 extends through the cross bar 68 and a collar 74 secures the bearing 66 in the cross bar 68 in a manner which permits the conductive bearing to freely rotate within the cross bar 68. A spring 72 extends between the cautery plug 70 and the conductive bearing 66, and provides a contact between the plug 70 and the bearing 66 regardless of the rotational position of the bearing 66. Movement of the spool member 52 relative to the stationary member 50 causes the snare 24 to extend from and retract into the distal end 16 of the sheath 12.

Referring to FIGS. 1 and 4, an electrically insulative extension sheath 80 extends over the shaft 18 between the proximal end 38 of the body 30 and the distal end 62 of the stationary member 50 coupled, e.g., via flare-nut connections 82, 84. Thus, there is a continuous outer connection joining, yet spacing apart, the distal handle assembly 26 and the proximal handle assembly 28. A stiffening sleeve 86 is preferably provided over the extension sheath 80 at the proximal end 38 of the body 30, and another stiffening sleeve 88 is preferably provided over the extension sheath 80 at the distal end 62 of the stationary member 50.

In use, the physician introduces the snare instrument 10 into the endoscope (not shown), typically by means of a port in the endoscope handle which communicates with the working channel of the endoscope. Then, the physician gives the proximal assistant's handle 28 to the assistant. The physician then grips the body 30 of the distal physician's handle 26 of the snare instrument and uses it to position the distal end 16 of the sheath 12 adjacent to the polyp to be excised. The physician then instructs the assistant to extend the snare, which is performed by moving the spool member 52 relative to the stationary member 50. The physician then uses the distal handle 26 to simultaneously axially position and rotate the snare over the polyp. Then, the physician instructs the assistant to close the snare and sever the polyp, using cautery if desired. In this manner, the physician controls the means of positioning the snare onto the polyp, and the assistant controls the opening and closing of the snare and the cauterization.

In the first embodiment, as discussed above, it will be appreciated that the knob 32 is preferably at least as long as the distance of movement needed to open and close the snare 24. However, turning now to FIGS. 5–7, according to a second embodiment of a snare instrument 110, the key 146 on the shaft 118 is made sufficiently small in diameter such that it can pass partly into the bearings 190, 191 on the body 130 (which support the knob 132) and proximal and distal ends 136, 138 of the body 130, or even into the sheath 112 and extension sheath 180, and their respective stiffening sleeves. Accordingly, the knob 132 is provided with a hollow knob shaft 192 having a non-circular bore 140 which rotatably engages the key 146 on the instrument shaft 118. The knob shaft 192 extends beyond the proximal and distal ends of the knob 132. The knob shaft 192 extends into bearings 190, 191 of the body 130 which allows the knob 132 and knob shaft 192 to spin within the body 130. The knob shaft 192 may optionally extend through the proximal and distal ends 136, 138 of the body 130, into the sheath (on the distal end) and into the extension sheath (on the proximal end). In this manner, it is possible to achieve a large range of axial motion (e.g., 3.5 inches) while having a knob 132 of much shorter dimension (e.g., 1.25 inches). It should be noted that if the key 146 has a substantial length (e.g., 0.75 inch), the body 130 and knob 132 can be made even shorter, since it is necessary for only a portion of the key 146 to be engaged with the non-circular bore 140 of the knob shaft 192 at any time.

Figure 9:
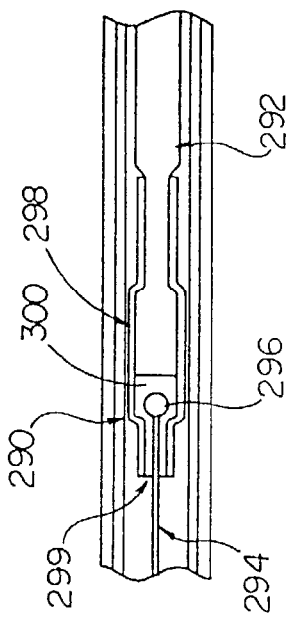
FIG. 9 is an enlargement of the area between lines 9a—9a and 9b—9b in FIG. 8.

In addition, while the first embodiment describes a shaft 18 that is monolithic and continuous from the snare 24 to the proximal handle assembly 28, the shaft may alternatively be a composite structure. Specifically, referring to FIGS. 8 and 9, according to a third embodiment of the invention, the straightened, torsionally-stiff, camber-free section of the shaft 218 need only extend from the snare to the knob 232. A swivel joint 290 may be interposed on the shaft 218 between the knob 232 and the proximal handle assembly, and join the shaft 218 to a flexible or stiff proximal shaft extension 292 which extends to the proximal handle assembly. The proximal end 294 of the shaft 218 is preferably formed into an enlarged section, i.e., a head 296, or a separate, enlarged head may be attached to the proximal end of the shaft. A swivel tube 298, preferably made of a malleable alloy, such as brass or stainless steel, is provided over the head 296. A distal end 299 of the swivel tube 298 is swaged or crimped to form a loose fit on the shaft 218, while being small enough to retain the head 296. The swivel tube 298 is placed onto the shaft 218 such that the head 296 is trapped inside the non-crimped portion 300 of the swivel tube 298. The extension shaft 292 is pushed into the proximal open end 304 of the swivel tube 298, and the swivel tube 298 is firmly crimped onto the extension shaft 292. The extension shaft 292 is preferably made of either a flexible cable, for example, a 1×7 stranded stainless steel cable preferably of 0.032-inch diameter, or a solid wire of a springy material such as stainless steel, for example, a 0.020-inch diameter 304 stainless steel spring-temper wire. The extension shaft 292 extends proximally from the swivel tube 298 to the spool so that it transmits reciprocating longitudinal motion of the spool through the swivel tube 298 to the shaft 218.

This variation in constriction of the extension shaft 292 is allowed because the purpose of the extension of the shaft 218 is merely to transmit the reciprocating axial motion imparted by the proximal handle; thus, if there exists a freely rotational joint between distal shaft 218 and the extension shaft 292, there is no requirement for the extension shaft to be straight, torsionally-stiff, or camber-free.

Figure 10:
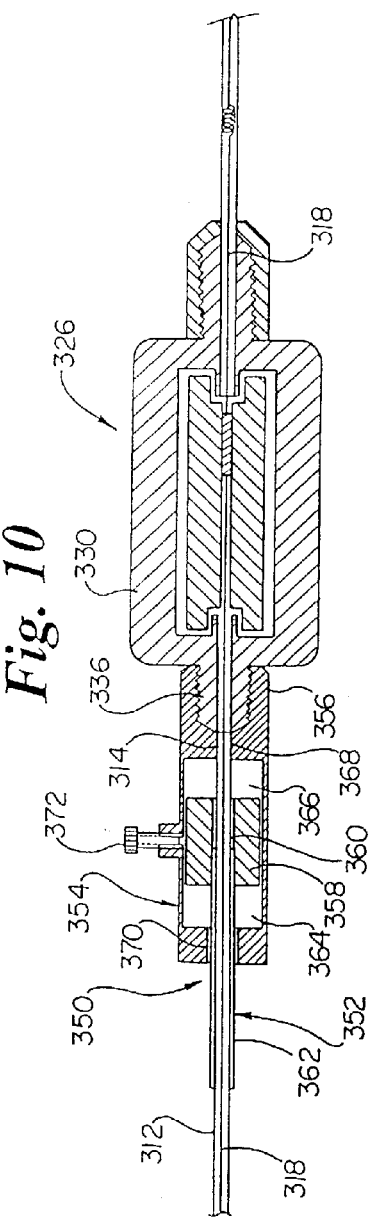
FIG. 10 is a broken section view of a fourth embodiment of the snare instrument of the invention.

Turning now to FIG. 10, according to a fourth embodiment of the invention, the distal handle assembly 326 includes a mount 350 capable of firmly coupling the distal handle assembly 326 to a port in an endoscope handle (not shown), for example, by interference fit. In a preferred configuration, the mount 350 includes a coupling fitting 352 which is couplable to the port of the endoscope, and a connector 354 which is slidably movable, yet capable of being secured in a position, relative to the coupling fitting 352. The connector 354 has a proximal end 356 which is threadably coupled to the distal end 336 of the body 330.

The coupling fitting 352 includes a cylindrical block 358 having an axial bore 360, and a tubular nosepiece 362 secured in the axial bore 360. The connector 354 includes a stepped bore 364 having a relatively large central portion 366, and relatively smaller proximal and distal portions 368, 370. The central portion 366 of the stepped bore 364 is sized to permit relative axial movement over the block 358. The distal portion 370 of the stepped bore 364 is sufficiently large to permit axial movement of the connector 354 over the nosepiece 362. A locking screw 372 extends radially into the central portion 366 of the stepped bore 364 of the connector 354 such that the screw 372 may be rotated to tighten against the block 358 to lock the connector 354 axially relative to the block. The proximal end 314 of the sheath 312 extends through the nosepiece 362 and block 358 and is fixedly coupled in the proximal portion 368 of the stepped bore 364. Other aspects of the fourth embodiment are substantially as described above with respect to the first embodiment.

In use, the snare instrument is inserted through a port of an endoscope until the nosepiece 362 of the snare instrument is stably inserted in the port. The distal end of the sheath of the snare instrument may then be adjustably fixed relative the distal end of the endoscope by adjusting the connector 354 (and hence the handle 326, shaft 318, and sheath 312) over the block 358. When the sheath is correctly positioned, screw 372 may be set. The distal handle 326 may then be operated, as described with respect to the first embodiment, to rotate the shaft 318 and snare relative to the sheath 312. Likewise, a proximal handle assembly, as described with respect to the first embodiment, may then be manipulated to longitudinally move the shaft 318 to open and close the snare (the sheath having been previously set in position). With the above-described embodiment, it may be possible for the physician to operate without an assistant as the axial placement of the snare instrument is established and set prior to rotation and activation of the snare loop.

Figure 11:
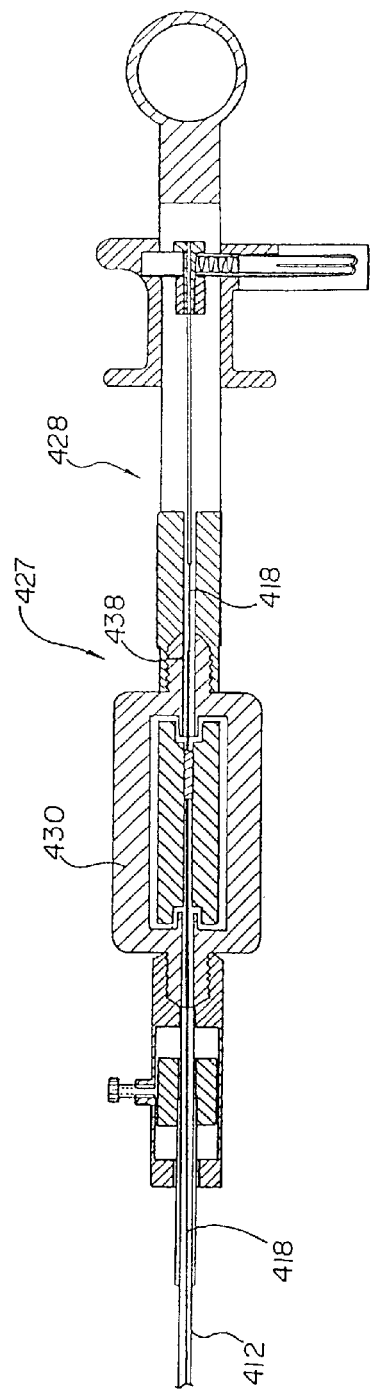
FIG. 11 is a broken section view of a fifth embodiment of the snare instrument of the invention.

Referring now to FIG. 11, according to a fifth embodiment of the invention, a single handle assembly 427 capable of being fixed relative to an endoscope handle is provided. The handle assembly 427 of the snare instrument includes all of the controls previously provided in the proximal and distal handle assemblies, and is substantially similar to the distal handle assembly 326, described above, with the additional incorporation of the snare opening and closing functions. To that effect, a sliding spool assembly 428 for longitudinally moving the shaft 418 relative to the sheath 412 may be substantially rigidly fixed to the proximal end 438 of the body 430. For example, a distal end 462 of a stationary member 450 of the spool assembly 428 may be threadably mated with the proximal end 438 of the body 430. The spool assembly is preferably otherwise substantially as described with respect to proximal handle assembly 28 of the first embodiment of the invention.

Figure 12:
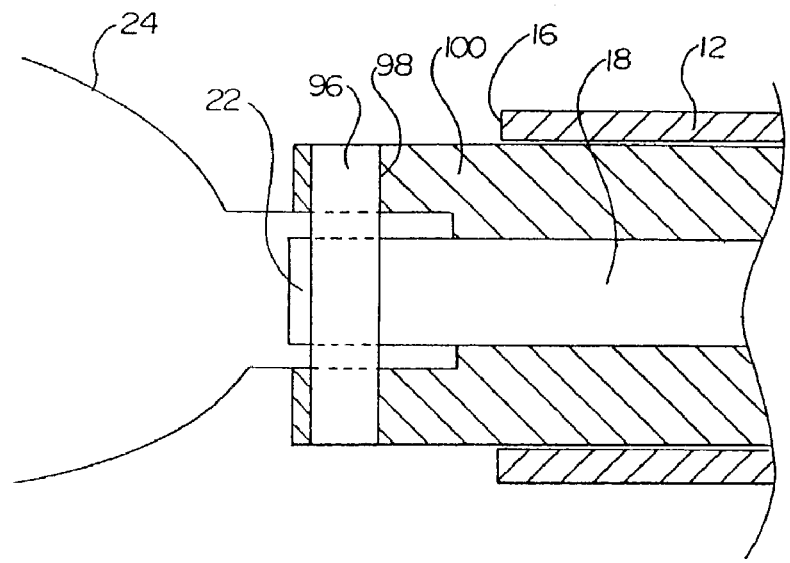
FIG. 12 is an enlarged view of a coupling member disposed at the distal end of the shaft.

Referring now to FIG. 12, the snare instrument 10 includes an elongate flexible tubular sheath 12 having a distal end 16, a flexible shaft 18 having a distal end 22 extending through and axially movable relative to the sheath 12, a snare 24 coupled to or formed at the distal end 22 of the shaft 18, preferably adjacent the distal end 16 of the sheath 12. In a preferred embodiment, a snare 24 can be coupled to the distal end 22 of the shaft 18 by a crimp band 96. Preferably, a coupling member 100 can be disposed at the distal end 22 of the shaft 18. In an exemplary embodiment, a coupling member 100 can be disposed over crimp band 96.

In a preferred embodiment, the coupling member 100 may comprise a shrink tube. In an exemplary embodiment, the coupling member 100 may have an outside diameter appropriate for fitting inside the sheath. Preferably, the coupling member 100 provides an increased ability to actuate an end effector, for example a snare 24.

Figure 13:
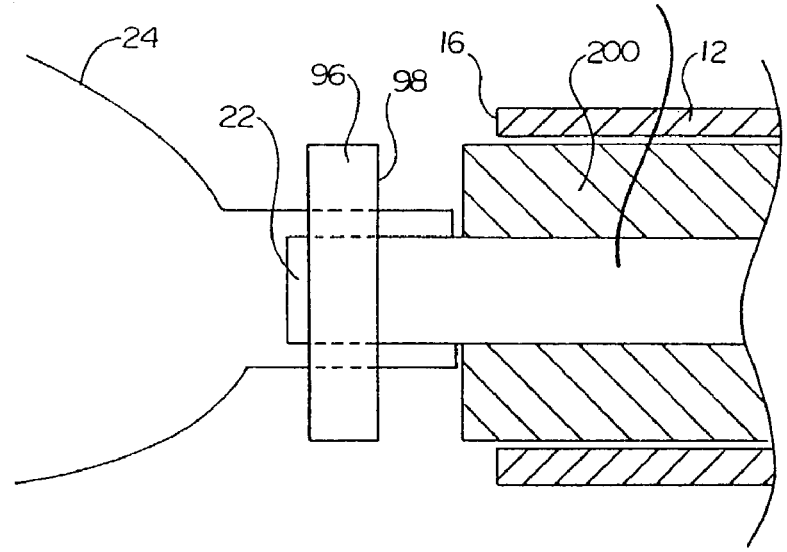
FIG. 13 is an alternate enlarged view of a coupling member disposed at the distal end of the shaft.

Referring now to FIG. 13, the snare instrument 10 includes an elongate flexible tubular sheath 12 having a distal end 16, a flexible shaft 18 having a distal end 22 extending through and axially movable relative to the sheath 12, a snare 24 coupled to or formed at the distal end 22 of the shaft 18, preferably adjacent the distal end 16 of the sheath 12. In a preferred embodiment, a snare 24 can be coupled to the distal end 22 of the shaft 18 by a crimp band 96. In an exemplary embodiment, crimp band 96 comprises a proximal end 98. Preferably, a coupling member 200 can be disposed at the distal end 22 of the shaft 18. In an exemplary embodiment, a coupling member 200 can be disposed proximal of the crimp band 96, for example just proximal of the proximal end 98 of the crimp band 96.

In a preferred embodiment, the coupling member 200 may comprise a shrink tube. In an exemplary embodiment, the coupling member 200 may have an outside diameter appropriate for fitting inside the sheath. Preferably, the coupling member 200 provides an increased ability to actuate an end effector, for example a snare 24.

The resulting device is fixedly couplable relative to an endoscopic handle and provides to the physician the following controls: a means for controllably advancing, retracting, and setting the sheath of the snare instrument relative to the distal end of the endoscope; a means for advancing (opening) and retracting (closing) the snare relative to the distal end of the sheath; and a means for steering (rotating) the snare to position the snare over a polyp. Since the physician has direct and immediate control of the entire instrument, the snare instrument obviates the need for an assistant during the procedure, and improves the speed and efficiency of the procedure.

There have been described and illustrated herein several embodiments of a surgical snare instrument. While particular embodiments of the invention have been described, it is not intended that the invention be limited thereto, as it is intended that the invention be as broad in scope as the art will allow and that the specification be read likewise. Thus, while the use of particular monolithic and composite shafts have been disclosed with respect to a snare instrument, it will be appreciated that other flexible shafts may also be provided. Also, while the cautery connector has been shown on the proximal handle, it will be appreciated that the cautery connection may be provided in the physician's handle, or elsewhere along the length of the device, provided that the cautery connection will not interfere with the axial longitudinal and rotating motions of the shaft. Furthermore, while particular shapes and configurations have been described with respect to the proximal and distal handles, it will be appreciated that other shapes and configurations may be provided therefor. As such, it will also be appreciated that other configurations which provide a gripping handle for the sheath, means for rotating the shaft, and means for longitudinally moving the shaft may be used. For example, a control knob which rotates about an axis perpendicular to the axis of the shaft via a right-angle drive (using two meshing bevel gears) may be used to rotate the shaft. The gears may be configured to permit step-up or step-down rotation, for example, such that rotation of the shaft rotates the shaft twice as much or one-half as much. In addition, levers, gears, friction wheels, pulleys, links, etc., may be used to longitudinally move the shaft within the sheath, and the snare relative to the distal end of the sheath. Moreover, while a particular nosepiece has been described for use in the fourth and fifth embodiment, it will be appreciated that other nosepieces enabling stable coupling of the snare handle to an endoscope handle may be used. For example, a threaded connector capable of threading into or over a port on the endoscope handle may be used. Also, in the fourth and fifth embodiment, the mount and the body may be integrally formed or molded, and in the fifth embodiment, the body and the proximal sliding spool assembly may be integrally formed or molded. In addition, it will be appreciated that aspects of the various embodiments may be combined. For example, but not by way of limitation, the key of the second embodiment or the swivel joint of the third embodiment may be used in either of the fourth and fifth embodiments. Furthermore, the described handle assemblies may be used with other surgical instruments where both axial and rotational movement of a control member relative to a tubular member is required. For example, the handle may be used in laparoscopic and endoscopic instruments, generally, which include an end effector other than a snare loop. For example, and not by way of limitation, end effectors such as baskets and forceps may be used with the handle. It will therefore be appreciated by those skilled in the art that yet other modifications could be made to the provided invention without deviating from its spirit and scope as claimed.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
   a tubular sheath having a lumen extending therethrough;
   a shaft slidably disposed in the lumen, the shaft including a proximal end and a distal end;
   an end effector disposed adjacent the distal end of the shaft and coupled to the shaft by a crimp band; and
   a coupling member coupled to the shaft and disposed proximally of the crimp band.

2. The medical device of claim 1, further comprising a first handle assembly for rotating the shaft relative to the sheath, and a second handle assembly for longitudinally moving the shaft relative to the sheath.

3. The medical device of claim 1, wherein the end effector comprises a snare loop.

4. The medical device of claim 1, wherein the coupling member comprises a shrink tube.

5. A medical device, comprising:
   a tubular sheath having a lumen extending therethrough and an inside diameter;
   a shaft disposed in the lumen;
   an end effector coupled to the shaft by a crimp band;
   a coupling member coupled to the shaft and disposed adjacent the crimp band, the coupling member having an outside diameter; and
   wherein the inside diameter of the sheath and the outside diameter of the coupling member are substantially equal so as to increase the ability to actuate the end effector.

6. The medical device of claim 5, further comprising a first handle assembly for rotating the shaft relative to the sheath, and a second handle assembly for longitudinally moving the shaft relative to the sheath.

7. The medical device of claim 5, wherein the end effector comprises a snare loop.

8. The medical device of claim 5, wherein the coupling member comprises a shrink tube.

9. The medical device of claim 5, wherein the coupling member is disposed over the crimp band.

10. The medical device of claim 5, wherein the coupling member is proximal of the crimp band.

11. The medical device of claim 5, wherein at least a portion of the coupling member is disposed within the sheath.

12. A medical device, comprising:
    a tubular sheath having a lumen extending therethrough;
    a shaft disposed in the lumen;
    an end effector coupled to the shaft by a crimp band;
    wherein the end effector is configured to shift between a first closed position wherein at least a portion of the end effector is disposed within the sheath and a second open position wherein the end effector is disposed distally of a distal end of the sheath;
    a coupling member coupled to the shaft and disposed adjacent the crimp band; and
    wherein at least a portion of the coupling member is disposed within the sheath when the end effector is in the second open position.

13. The medical device of claim 12, further comprising a first handle assembly for rotating the shaft relative to the sheath, and a second handle assembly for longitudinally moving the shaft relative to the sheath.

14. The medical device of claim 12, wherein the end effector comprises a snare loop.

15. The medical device of claim 12, wherein the coupling member comprises a shrink tube.

16. The medical device of claim 12, wherein the coupling member is disposed over the crimp band.

17. The medical device of claim 12, wherein the coupling member is proximal of the crimp band.

18. A medical devices, comprising:
    a tubular sheath having a lumen extending therethrough;
    a shaft disposed in the lumen;
    a first handle assembly for rotating the shaft relative to the sheath;
    a second handle assembly for longitudinally moving the shaft relative to the sheath;
    a snare coupled to the shaft by a crimp band; and
    a shrink tube coupled to the shaft and disposed adjacent the crimp band, the shrink tube being arranged and configured to increase the ability to actuate the snare.

19. A medical device, comprising:
    a flexible tubular sheath having a lumen extending therethrough;
    a shaft disposed in the lumen, the shaft being rotatable and longitudinally moveable within the sheath;
    a first assembly for rotating the shaft relative to the sheath;
    a second assembly for longitudinally moving the shaft relative to the sheath;
    a snare coupled to the shaft by a crimp band; and
    a coupling member coupled to the shaft and disposed adjacent the crimp band and within the lumen of the sheath.

20. The medical device of claim 19, wherein the coupling member comprises a shrink tube.

21. The medical device of claim 19, wherein the coupling member is disposed over the crimp band.

22. The medical device of claim 19, wherein the coupling member is disposed proximally of the crimp band.

* * * * *

UNITED STATES PATENT AND TRADEMARK OFFICE
CERTIFICATE OF CORRECTION

PATENT NO.    : 6,972,017 B2
DATED         : December 6, 2005
INVENTOR(S)   : Kevin W. Smith et al.

It is certified that error appears in the above-identified patent and that said Letters Patent is hereby corrected as shown below:

Column 6,
Line 44, delete "constriction" and insert -- construction --.

Signed and Sealed this

Sixteenth Day of May, 2006

JON W. DUDAS
*Director of the United States Patent and Trademark Office*